United States Patent [19]
Yates et al.

[11] Patent Number: 5,230,333
[45] Date of Patent: Jul. 27, 1993

[54] THERMAL SOCK HAVING A TOE HEATING POCKET

[76] Inventors: James W. Yates, Rte. 1, Box 585; Ronnie L. Yates, Box 3441, both of Wise, Va. 24293

[21] Appl. No.: 888,646

[22] Filed: May 27, 1992

[51] Int. Cl.[5] .............................................. A61F 7/00
[52] U.S. Cl. ........................................ 128/382; 2/239; 128/402
[58] Field of Search ............... 128/382, 399, 400, 402, 128/403; 126/204; 2/239; 36/2.6, 10

[56] References Cited

U.S. PATENT DOCUMENTS

| | | | |
|---|---|---|---|
| 1,970,081 | 8/1934 | Eisendrath | 128/402 |
| 2,792,827 | 5/1957 | Gravin | 126/204 |
| 3,017,640 | 1/1962 | Cardwell | 2/239 |
| 3,293,405 | 12/1966 | Costanzo | 2/239 |
| 3,476,102 | 11/1969 | Sarnoff | 126/204 |
| 4,023,282 | 5/1977 | Ziegelheafer | 36/2.6 |
| 4,055,108 | 10/1977 | Pelton | 128/403 |
| 4,094,080 | 6/1978 | Sanders | 36/2.6 |
| 4,249,319 | 2/1981 | Yoshida | 36/2.6 |
| 4,676,223 | 6/1987 | Petersen | 128/204 |
| 4,841,646 | 6/1989 | Maurer | 126/204 |
| 4,961,235 | 10/1990 | Williger | |
| 5,027,440 | 7/1991 | Morris | 2/239 |
| 5,038,779 | 8/1991 | Barry et al. | |

FOREIGN PATENT DOCUMENTS 3544856  10/1986  Fed. Rep. of Germany ......... 36/2.6

OTHER PUBLICATIONS

"Visa-Therm Socks Powered by D-Cells", The Sporting Goods Dealer, Aug. 1966, p. 222.

Primary Examiner—Mark S. Graham
Attorney, Agent, or Firm—Laubacher & Laubacher

[57] ABSTRACT

A thermal sock includes on the top part of the toe portion of the sock a pocket for receiving a chemical heating pouch, thereby to effect warming of the toes of a user. A pocket is defined by a fabric layer that is secured to the sock by a generally U-shaped line of stitching. A closure arrangement, such as a cooperating pair of Velcro strips, a button, a snap fastener device or the like, may be provided for closing the flap defined on the fabric layer at the open end of the pocket.

8 Claims, 1 Drawing Sheet

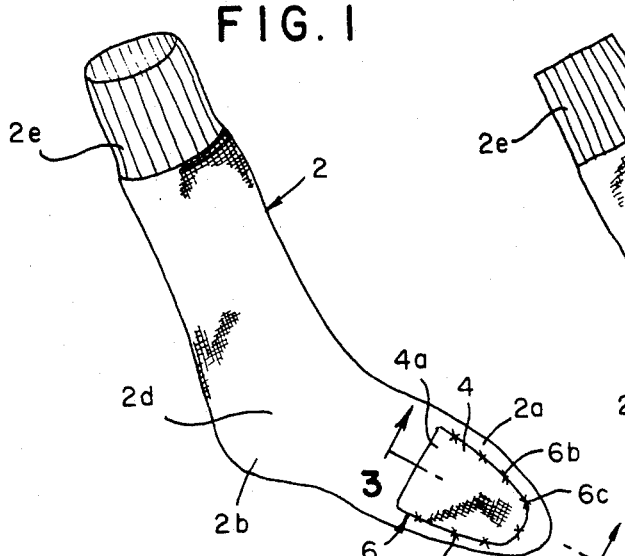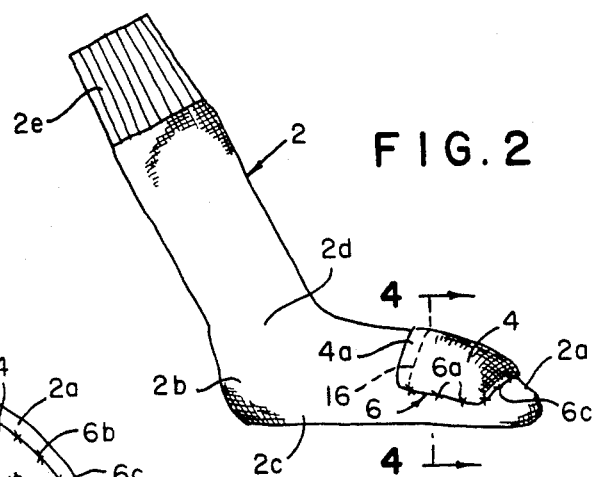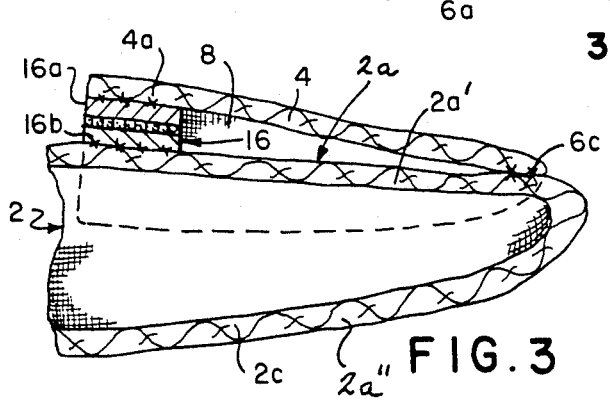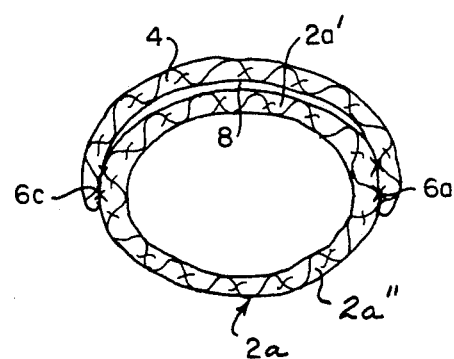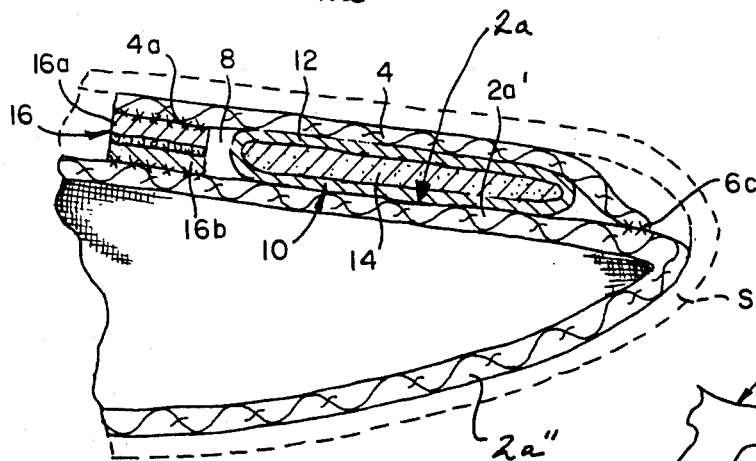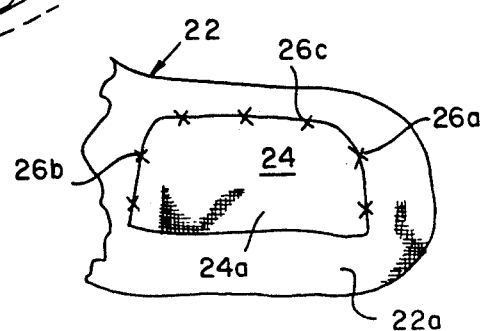

THERMAL SOCK HAVING A TOE HEATING POCKET

FIELD OF THE INVENTION

A thermal sock for hunting, skiing, or stadium use, or the like is provided having a pocket on the sock toe portion for receiving a chemical heating pouch, thereby to heat the user's toes.

BRIEF DESCRIPTION OF THE PRIOR ART

As indicated by the advertisement of Visa-Therm Products that appeared on Page 222 of the August 1966 issue of *The Sporting Goods Dealer*, it has been proposed to provide wool/nylon socks that are electrically heated by a D-cell battery associated with each sock. When rechargeable batteries are used, heat may be provided for up to five hours.

In the Barry et al U.S. Pat. No. 5,038,779, it has been proposed to provide a therapeutic garment, such as a vest or the like, for applying cold or heat to a desired localized portion of the user's body, specifically, the user's back. A pocket is formed for receiving a thermal control packet that is cooled to a given temperature in a freezer, or is heated in a microwave oven if heat therapy is desired. The position of the pocket is adjustable on the user's back, thereby to permit the application of therapy to the specific portion of the lower back that is in pain.

Finally, as shown by the patent to Williger U.S. Pat. No. 4,961,235, it is known to provide a compartment in the ribbed calf portion of a sock, thereby to permit the user to carry a key, coins or the like, which pocket is provided with closure means such as a zipper, button, Velcro fastener or the like.

The present invention was developed to provide an improved thermal sock construction for warming the toes of the user by means of a chemical heating pouch inserted into a pocket formed on the top of the toe portion of the sock.

SUMMARY OF THE INVENTION

Accordingly, it is a primary object of the present invention to provide a thermal sock including on the top part of the sock toe portion a pocket for receiving a chemical heating pouch, thereby to warm the toes of the user.

According to a more specific object of the invention, the pocket is defined on the upper part of the sock toe portion by means of a fabric layer that is stitched or adhesively secured to the sock by a generally U-shaped line of attachment. The stitching or other line of attachment extends solely between the upper surface of the toe top part and the fabric layer, thereby to isolate the line of attachment from the toes of the user, whereby rubbing and blistering of the toes by the stitching is avoided.

A further object of the invention is to provide closure means for closing the fabric flap portion that defines the pocket opening. In the preferred embodiment, the pocket closure means includes a pair of cooperating Velcro strips, although other types of closure means, such as a button arrangement, a zipper or a snap fastener, could be used as well.

Another object of the invention is to provide a thermal sock including an elastic ribbed portion for engagement with the calf of the user, whereby the sock is positively oriented on the user's foot with the pocket adjacent the upper surface of the user's toes. In one embodiment, the access opening to the pocket extends normal to the longitudinal axis of the sock, while in another embodiment, the pocket access opening extends parallel with the sock longitudinal axis.

The thermal sock is a garment designed solely for the purpose of foot warming. The pouch, which is sewn on the top of the toe portion of the sock may be formed of the same fabric as the actual sock and therefore will not cause the wearer any discomfort. Most of the sock owners will be wearing a boot of some sort which also allows for more room in the toe area.

The pouch is arranged on the top of the sock namely for comfort. Another benefit of having the pouch and warmer on the top is that as the foot perspires, the moisture does not effect the heating capability of the warmer. The opening to the pouch may be provided at any edge, as desired. The sock is suitable for use by adults or children. For use as a hunting sock, the fabric would normally include a wool and polypropylene blend, and would be worn with hunting boots. For use as a ski sock, an Orlon-wool-nylon blend sock would be worn when used as a stadium spectator sock, and a cotton blend sock would be suitable for use as a utility sock by outdoor laborers, farmers and cold weather workers.

BRIEF DESCRIPTION OF THE DRAWING

Other object and advantages of the invention will become apparent from a study of the following specification, when viewed in the light of the accompanying drawings, in which:

FIG. 1 is a perspective view of the heated sock of the present invention;

FIG. 2 is a side elevation view of the sock;

FIG. 3 is a sectional view taken along line 3—3 of FIG. 1;

FIG. 4 is a sectional view taken along line 4—4 of FIG. 2;

FIG. 5 is a sectional view corresponding with FIG. 3, illustrating the manner of insertion of the heating pouch into the pocket; and FIG. 6 is a modification of the embodiment of FIGS. 1-5.

DETAILED DESCRIPTION

Referring first more particularly to FIGS. 1 and 2, the thermal sock 2 of the present invention is formed of a relatively thick knitted fabric material—such as wool, a synthetic fiber/wool or cotton-polypropylene blend, or the like—as normally used in hiking and skiing socks. The sock includes a toe portion 2a, a heel portion 2b, a sole portion 2c, an ankle portion 2d, and an elastic ribbed calf portion 2e. In accordance with a characterizing feature of the invention, a fabric layer 4 is secured to the top part 2a' of the sock toe portion 2a by a generally U-shaped (but not limited to) line of stitching 6 to define a pocket 8 for receiving a conventional oxygen-activated chemical heating pouch 10, as shown in FIG. 5. One example of a commercially available heating pouch is the MEDIHEAT product produced by Heatmax, Inc. of Dalton, Ga., having a porous cover layer 12 containing an oxygen-activated mixture 14 including activated charcoal, iron powder, saltwater and wood fibers. This heating pouch normally has an operating life of about 6 hours. As shown in FIG. 3, the bottom part 2a" of the toe portion of the sock merges with the sole portion 2c.

The pocket-defining fabric layer 4 (formed, for example, from 100% polyester) is stitched solely to the upper extremity of the top part 2a' of the sock toe portion 2a by a generally U-shaped but not limited to) line of stitching 6 having a pair of parallel side portions 6a, 6b and a transverse bottom portion 6c, thereby to define the pocket 8. As shown in FIGS. 3 and 5, no portion of the stitching 6 extends completely through the upper part of the toe portions of the sock, thereby to isolate the inner surface of the sock from the stitching and thus avoid rubbing and blistering of the user's toes. The U-shaped line of stitching 6 defines an unstitched flap portion 4a which forms an opening through which the heating pouch 10 is inserted into the pocket 8. If desired, a pair of cooperating Velcro (i.e., hook and loop fastener) strips 16a and 16b may be fastened to the fabric layer 4 and the top part 2a' of the sock toe portion 2a, respectively, thereby to provide means for closing the pocket. Alteratively, button, snap or other closure means may be provided. Of course, in certain cases the provision of pocket closure means may be completely avoided, the dimensions of the pocket being sufficient to retain the heating pouch in place.

In the embodiment of FIGS. 1-5, the stitching bottom portion 6c is arranged adjacent the forward extremity of the toe portion of the sock, and the pocket flap portion 4a extends transversely across the upper surface of the toe portion of the sock. In the embodiment of FIG. 6, the pocket fabric layer 24 is rotated through 90° relative to the sock, so that the bottom portion 26c of the U-shaped stitching and the open flap portion 24a extend in the direction expending between the heel and toe portions of the sock.

In operation, either before or after the user applies a sock upon his foot, the pocket flap 4a is opened and the heating pouch is inserted within the pocket 8, thereby to heat the user's toes for a period of from about 6 to 8 hours. The user then in a normal manner introduces his or her foot into the associated boot or shoe S (FIG. 5), whereby the user's toes will be heated for the operating life of the pouch. Of course, if the user wishes to discontinue the heating operation at any time, he merely removes his foot from
the shoe or boot, and opens the flap 4a, whereupon the pouch 10 is slipped out of the pocket. If the pocket is provided with the Velcro closure means, the components 16a and 16b are merely manually separated to open the flap 4a, and are subsequently automatically re-fastened together when the pocket is closed. The ribbed portion 2e of the sock serves to properly orient the sock on the user's foot with the pocket 8 above the user's toes.

While the line of attachment has been illustrated and described as being generally U-shaped, it is apparent that other configurations for defining a pocket are equally possible. Moreover, instead of a line of stitching, the line of attachment could be an adhesive attachment as well. The pouch could be arranged with its opening extending in any direction, as desired.

While in accordance with the provisions of the Patent Statutes the preferred forms and embodiments of the invention have been illustrated and described, it will be apparent that the various changes may be made without deviating from the inventive concepts set forth above.

What is claimed is:

1. A sock for heating the toes of the foot of a user by means of a heating pouch containing an oxygen-activated chemical heating agent, comprising:
   (a) a sock body formed of fabric and having at least toe (2a), heel (2b), sole (2c), and ankle (2d) portions, said toe portion including a bottom part (2a") that merges with said sole portion, and a top part (2a') arranged above said bottom part; and
   (b) pocket means adapted for mounting the heating pouch on said toe portion top part, said pocket means including:
      (1) a layer of fabric having a center portion and an edge portion; and
      (2) generally U-shaped means securing part of said layer edge portion to said toe portion top part, thereby to define a pocket (4) adapted for receiving the heating pouch, an unsecured portion of said fabric layer defining a flap portion (4a, 24a) forming an access opening to said pocket;
      (3) said U-shaped securing means being isolated from the surface of said toe portion top part that is adjacent said toe portion bottom part, whereby rubbing and blistering of the toes of the user are avoided.

2. A sock as defined in claim 1, wherein said securing means comprises a generally U-shaped line of stitching (6) defining side (6a, 6b) and bottom (6c) edges of said pocket.

3. A sock as defined in claim 2, wherein said flap portion (4a) extends generally normal to the direction extending between said heel and toe portions of said sock body, said pocket being so oriented on said sock body that the stitching portion (6c) defining the bottom edge of said pocket is remote from said ankle portion.

4. A sock as defined in claim 2, wherein said flap portion (24a) extends generally parallel with the direction extending between the heel and toe portions of said sock body.

5. A sock as defined in claim 2, and further including closure means (16) for fastening said fabric layer flap portion with said top part of said sock toe portion.

6. A sock as defined in claim 5, wherein said closure means includes a pair of cooperating hook and loop fastener layers secured with said flap portion and with said toe portion top part, respectively.

7. A sock as defined in claim 3, wherein said sock has a resilient ribbed calf portion (2e) on the opposite side of said ankle portion from said toe portion, thereby to assist in properly orienting the sock on the user's foot with said pocket arranged above the user's toes.

8. A sock for heating the toes of the foot of a user by means of a heating pouch containing an oxygen-activated chemical heating agent, comprising:
   (a) a sock body formed of fabric and having at least toe (2a), heel (2b), sole (2c), and ankle (2d) portions, said toe portion including a bottom part (2a") that merges with said sole portion, and a top part (2a') arranged above said bottom part; and
   (b) pocket means adapted for mounting the heating pouch on said sock toe portion top part, said pocket means including:
      (1) a layer of fabric having a center portion and an edge portion; and
      (2) generally U-shaped line of stitching (6) securing part of said layer edge portion to said toe portion top part, thereby to define a pocket (4) adapted for receiving said pouch;

(3) said line of stitching defining side (6a,6b) and bottom (6c) edges of said pocket, and an unsecured portion of said fabric layer defining a flap portion (4a) forming an access opening to said pocket;

(4) said U-shaped line of stitching being isolated from the surface of said toe portion top part that is adjacent said toe portion bottom part, whereby rubbing and blistering of the toes of the user are avoided.

* * * * *